US008547231B2

(12) United States Patent
Schermeier et al.

(10) Patent No.: US 8,547,231 B2
(45) Date of Patent: Oct. 1, 2013

(54) MEDICAL SYSTEM

(75) Inventors: Olaf Schermeier, Lübeck (DE); Gerd Wotha, Warnsdorf (DE); Andreas Otto, Bargteheide (DE)

(73) Assignee: Drager Medical GmbH, Lubeck (DE)

( * ) Notice: Subject to any disclaimer, the term of this patent is extended or adjusted under 35 U.S.C. 154(b) by 913 days.

(21) Appl. No.: 12/517,144

(22) PCT Filed: Jun. 28, 2007

(86) PCT No.: PCT/EP2007/005738
§ 371 (c)(1),
(2), (4) Date: Jun. 1, 2009

(87) PCT Pub. No.: WO2008/064725
PCT Pub. Date: Jun. 5, 2008

(65) Prior Publication Data
US 2011/0001611 A1 Jan. 6, 2011

(30) Foreign Application Priority Data
Dec. 1, 2006 (DE) .......................... 10 2006 056 723

(51) Int. Cl.
G06K 7/01 (2006.01)

(52) U.S. Cl.
USPC .......................... 340/572.1; 600/481; 600/301

(58) Field of Classification Search
USPC .................. 340/10.1, 10.5, 10.51, 10.6, 10.2, 340/10.3, 572.1, 573.1
See application file for complete search history.

(56) References Cited

U.S. PATENT DOCUMENTS

| | | | |
|---|---|---|---|
| 7,062,251 B2 * | 6/2006 | Birkett et al. | 455/400 |
| 2001/0051766 A1 * | 12/2001 | Gazdzinski | 600/309 |
| 2004/0039263 A1 | 2/2004 | Bardy | |
| 2006/0026205 A1 | 2/2006 | Butterfield | |
| 2007/0075840 A1 * | 4/2007 | Brandt et al. | 340/10.41 |

FOREIGN PATENT DOCUMENTS

| | | |
|---|---|---|
| EP | 1 731 089 | 12/2006 |
| EP | 1 731 188 | 12/2006 |
| WO | WO 2004/079554 | 9/2004 |
| WO | WO 2005/082452 | 9/2005 |
| WO | WO 2005/112744 | 12/2005 |
| WO | WO 2007/059810 | 5/2007 |

OTHER PUBLICATIONS

International Search Report for PCT/EP2007/005738, mailed Feb. 20, 2008.
Yang et al., "Security and Privacy in RFID and Applications in Telemedicine", IEEE Communications Magazine, Apr. 2006, pp. 64-72, XP002468207.

* cited by examiner

*Primary Examiner* — Jennifer Mehmood
*Assistant Examiner* — Yong Hang Jiang
(74) *Attorney, Agent, or Firm* — Nixon & Vanderhye P.C.

(57) ABSTRACT

The invention relates to a medical system (1) with a monitoring station (3) and at least one medical work station (5, 7). The medical work station (5, 7) is designed to gather physiological data of a patient (4). The invention is characterized in that the at least one medical work station (5, 7) comprises a respiratory device (43, 60) with a connection (49, 51, 72, 74) for a respiratory hose (53, 57). The medical work station (5, 7) comprises a radio frequency detection unit (45, 68), which is designed for detecting a radio frequency marking (55) connected with a respiratory hose in the region of the connection for a respiratory hose, and to create a marking signal, representing the marking information. The medical system (1) is designed to associated the physiological data and the patient data, particularly the data set representing the physiological data and the patient data set, with each other, as a function of the marking signal.

8 Claims, 2 Drawing Sheets

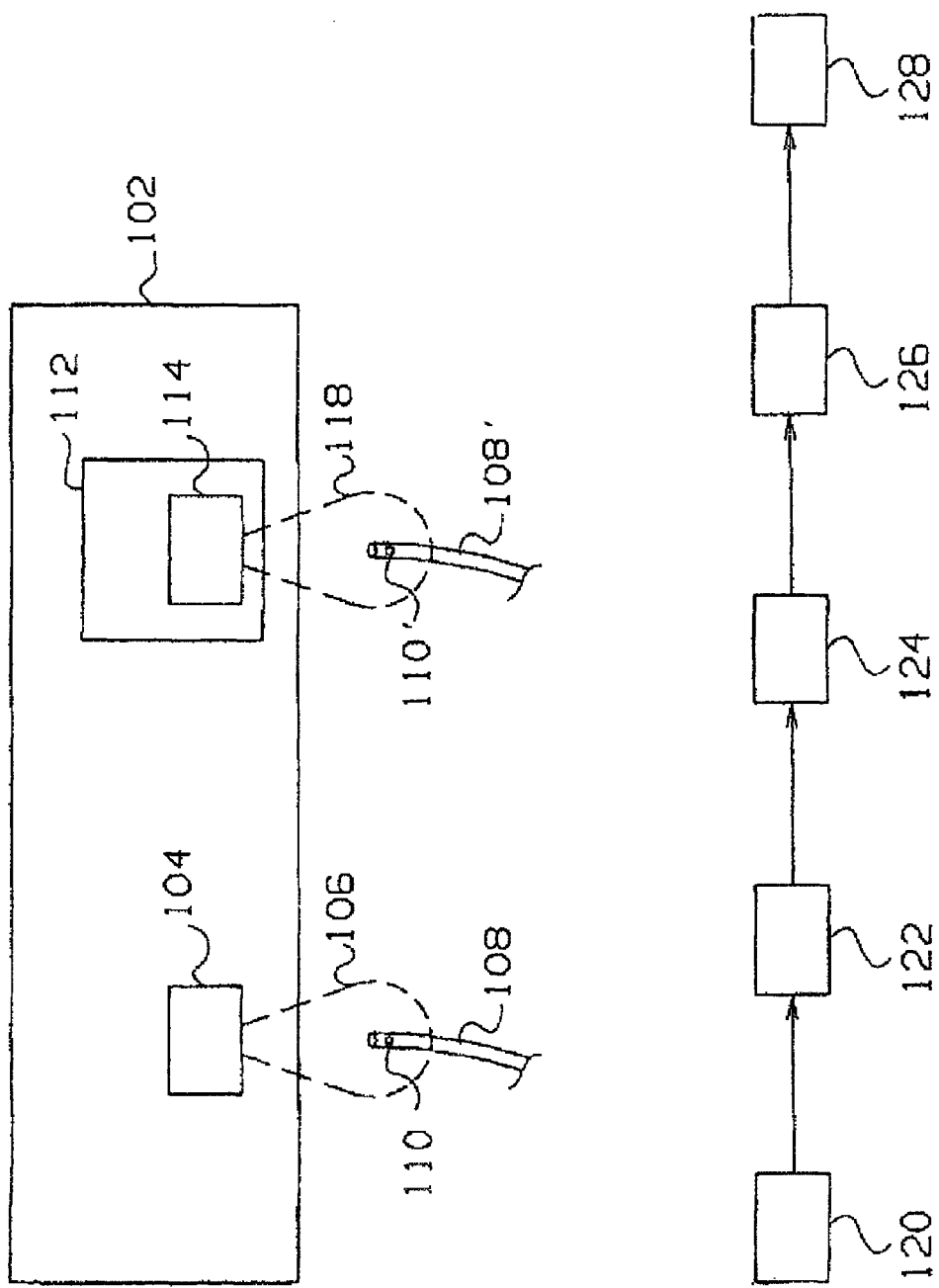

MEDICAL SYSTEM

This application is a National Phase of International Application No. PCT/EP2007/005738, filed 28 Jun. 2007, which claims priority to German Application No. 10-2006-056723.4, filed 1 Dec. 2006, the entire contents of each of which are hereby incorporated by reference.

The invention relates to a medical system with a monitoring station and with at least one medical workstation. The at least one medical workstation is designed to acquire physiological data of a patient. The at least one medical workstation is operatively connected to the monitoring station and is designed to generate a data signal representing the physiological data and to send said signal to the monitoring station. The monitoring station is designed to receive the data signal. The monitoring station has a memory for at least one patient data record representing patient data and at least one display unit for displaying the physiological data and the patient data. The medical system is designed to assign the patient data and the physiological data to one another.

In the case of medical systems known from the prior art, the patient data and the physiological data must be assigned to one another by a user. Assignment errors are possible during this assigning by a user.

The object on which the invention is based therefore is to specify a medical system which makes improved assignment possible and to specify a method for assigning patient data to physiological data.

The medical system of the type mentioned initially comprises a medical workstation with a respiratory device and a connection for a respiratory tube. The respiratory device has a radiofrequency detection device which is designed to detect a radiofrequency marker with marker information connected to a respiratory tube in the region of the connection for the respiratory tube and to generate a marker signal representing the marker information. The medical system is designed to acquire the physiological data using a monitor and to assign the patient data, in particular a data record corresponding to the data signal, and the patient data record to one another, depending on the marker signal. A medical system with a respiratory device and a radiofrequency detection device can advantageously unambiguously and reliably assign acquired physiological data to patient data.

An advantageous embodiment of the medical system also comprises at least one respiratory tube with a radiofrequency marker, the radiofrequency marker representing marker information. By way of example, to this end, the radiofrequency marker can readably retain the marker data record representing the marker information.

In a preferred embodiment, the radiofrequency marker has a random access memory for the marker data record which represents the marker information and contains at least patient data as marker information.

Advantageously, this affords the possibility of a respiratory tube retaining personal patient data such that it is possible to reliably assign the patient data to the physiological data acquired from the patient. When a patient is, for example, transported from one medical workstation to another medical workstation in an intensive care unit of a hospital, the patient can carry the respiratory tube with the patient data. Once the patient has been transported to another medical workstation, the respiratory tube is connected to said other medical workstation. The other medical workstation can thereupon detect the radiofrequency marker; read out the marker data record and generate a marker signal which represents the patient data; and, after the respiratory tube has been connected, send the acquired physiological data of the patient together with the marker information to the monitoring station. This makes it possible to precisely assign the physiological data to the patient data.

In a preferred embodiment, at least one medical workstation is designed to generate a data record with physiological data and/or detection parameters for acquiring physiological data and to transfer said data record to the radiofrequency marker by means of the radiofrequency detection device and save it on said marker. It is furthermore preferred for the medical workstation to be designed to read out the data record comprising physiological data and/or detection parameters for acquiring physiological data and saved in the radiofrequency marker, by means of the radiofrequency detection device. This advantageously makes it possible for the medical workstation to carry out or continue a further operation, for example a respiratory process, depending on the read out detection parameters and/or the read out physiological data.

It is preferable for the medical workstation to be capable of advantageously sending the read out physiological data, acquired by way of example by another medical workstation, to the monitoring station. Exemplary embodiments of physiological data are an oxygen proportion or a carbon dioxide proportion of a respiratory gas flow or a minute ventilation.

Exemplary embodiments of a respiratory device of a medical workstation are a respirator or an anesthetic ventilator.

The respiratory device is designed to generate inspiration or expiration. To this end, the respiratory device has a ventilation device and a connection for a respiratory tube connected at least indirectly to said ventilation device. The respiratory device preferably has at least one gas sensor and is designed to acquire physiological data, in particular respiratory data of a patient connected to the respiratory device, by means of the gas sensor. The gas sensor is, for example, an oxygen sensor or a carbon dioxide sensor which is designed in each case to detect a gas proportion of a respiratory gas flow, in particular oxygen or carbon dioxide, respectively, and generate a gas proportion signal representing the gas proportion. The respiratory device can more preferably have a minute ventilation sensor which can detect a minute ventilation of the respiratory gas flow and can generate a minute ventilation signal representing the minute ventilation. The respiratory device is preferably designed to generate a data record corresponding to the gas proportion signal and/or the minute ventilation signal and thus representing physiological data of the patient.

In a preferred embodiment of the medical system, at least one medical workstation is wirelessly connected to the monitoring station. At least one further medical workstation can be connected to the monitoring station by wires. Exemplary embodiments of a wireless connection of a medical workstation to the monitoring station include a WLAN connection, a Bluetooth connection, a radio connection, an optical connection, in particular an infrared connection such as an IrDA (Infrared Data Association) connection. To this end, the medical workstation can have a transmitter appropriate for the wireless connection type. The medical system has a receiver which is appropriate for the wireless connection type and which is connected to the monitoring station. In this fashion, a monitoring station together with at least two medical workstations can form a medical system comprising a network of medical workstations.

Exemplary embodiments of a medical system with a wired connection between the monitoring station and the at least one medical workstation include a LAN (Local Area Network) connection, a serial connection, by way of example a USB connection, or a fast connection, in particular a high-speed interface.

In an advantageous embodiment, the radiofrequency marker has a random access memory for a data record representing the marker information and for further data. The further data can be, for instance, the physiological data, represented by an appropriate data record.

Preferred embodiments of a radiofrequency detection device are designed to operate in a frequency range from 30 kilohertz to 500 kilohertz, in a frequency range from 800 to 950 megahertz, or in a frequency range from 1 gigahertz to 3 gigahertz. The radiofrequency detection device is preferably designed to be operated at a frequency of 125 kilohertz or at a frequency of 13.56 megahertz. The radiofrequency detection device and the radiofrequency marker can, when transmitting a marker signal representing the marker information, for example, be operated using one of the following modulation methods or a combination of the following modulation methods:

FM (frequency modulation)
AM (amplitude modulation)
FSK (frequency shift keying)
ASK (amplitude shift keying)
PSK (phase shift keying)

The radiofrequency detection device can preferably detect the radiofrequency marker by load modulation. In the process, the radiofrequency detection device can supply transmission energy to the radiofrequency marker. By way of example, it is possible for the radiofrequency marker to have an energy store to this end and store the received transmission energy and utilize the latter to send back an answer transmission signal representing the marker information.

In an advantageous embodiment, the radiofrequency marker is an active radiofrequency marker which has an energy source for sending the marker information.

The invention also relates to a respiratory tube to be connected to a respiratory device. The respiratory tube has a radiofrequency marker with marker information. Such a respiratory tube can advantageously be assigned to a patient.

In an advantageous embodiment, the radiofrequency marker has a random access memory for patient data. More preferably, the random access memory is designed to retain physiological data. For example, to this end said memory has a size of at least 50 kilobytes, preferably 500 kilobytes. Advantageously, the radiofrequency marker has a memory controller connected to the random access memory. This advantageously makes it possible to correctly assign physiological data to patient data in a medical system.

In an advantageous embodiment of the medical system, the medical workstation is designed to save, in a random access memory of a radiofrequency marker of a respiratory tube and in a fashion that can be repeatedly read out, a data record representing detection and/or equipment parameters of the medical workstation by means of the radiofrequency detection device.

The medical workstation is preferably designed to again read out the data record, saved on the radiofrequency marker, when a respiratory tube is connected to the medical workstation, by means of the radiofrequency detection device and to carry out further acquisition of physiological data depending on the read out parameters. This makes it possible to advantageously save the adjustment and equipment parameters required to operate a medical workstation and, in particular, generated individually for a patient on the radiofrequency marker of the respiratory tube. If a patient is transported to a different medical workstation which, for example, is arranged in a different treatment room, the different medical workstation can continue to operate there using those operational and/or equipment parameters which were previously saved on the radiofrequency marker of the respiratory tube.

Operational parameters can, for example, include a quantity or concentration of anesthetics to be administered.

The invention also relates to a method for assigning patient data to physiological data. This method acquires physiological data of a patient. In a further step, the acquired physiological data are assigned to retained patient data. In a further step, the physiological data and the patient data are rendered together, in particular visually or audibly. The method advantageously acquires marker information of a respiratory tube and the patient data and the physiological data are rendered, assigned to one another, depending on the marker information. In a preferred embodiment of the respiratory tube, the marker information represents the patient data.

A display unit of a medical system can comprise an image rendering unit. A display unit of a medical system can have a display, in particular a liquid crystal display, at least one lamp, in particular a light-emitting diode, or an acoustic rendering unit. The monitoring station of the medical system can advantageously display the physiological data by means of the at least one lamp, by means of the acoustic rendering unit, or by means of the image rendering unit. The monitoring station can display the patient data by means of the display or by means of the image rendering unit together, in particular temporally together, with the physiological data.

The invention will now be described in the following text with reference to the figures and further exemplary embodiments.

FIG. 2 shows an exemplary embodiment of a method for assigning patient data to physiological data.

Figure 1:
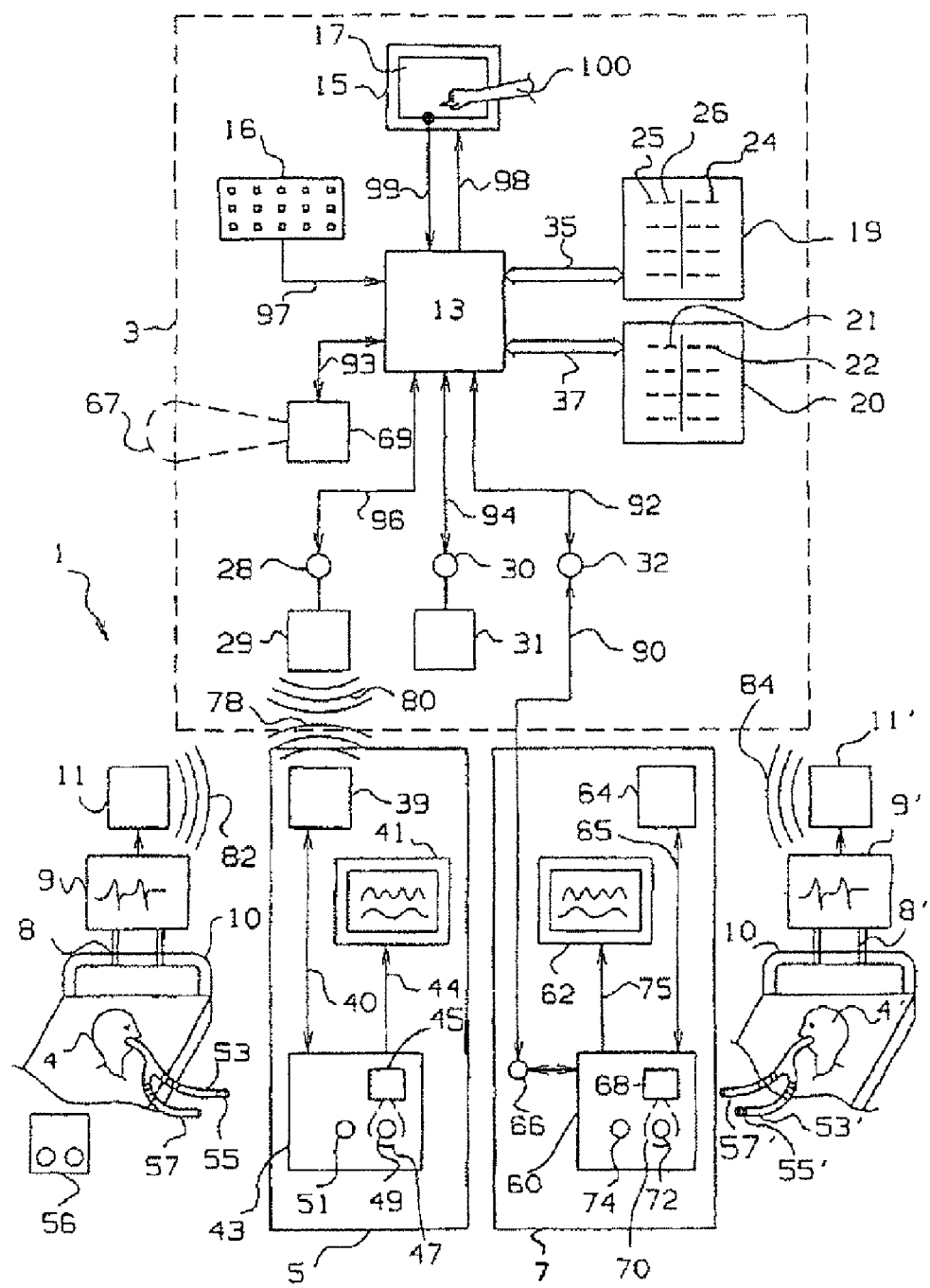
FIG. 1 shows an exemplary embodiment of a medical system with two medical workstations.

FIG. 1 schematically shows an exemplary embodiment of a medical system 1. The medical system 1 has a monitoring station 3, a medical workstation 5, and a medical workstation 7. The medical workstations 5 and 7 are respectively designed to acquire physiological data of a patient 4. The medical system 1 also has a medical monitor 9 which is designed to acquire physiological data, in particular an electrocardiogram of the patient 4. On its output side, the medical monitor 9 is connected to an interface 11 which is designed to send the acquired patient data wirelessly in the form of wirelessly sent data 82 to the medical workstation 5. The monitoring station 3 has a central processing unit 13, a display unit 15 designed as an image rendering unit, and a touch-sensitive surface 17. The monitoring station 3 also has a lookup memory 19 and a lookup memory 20. The lookup memory 19 and the lookup memory 20 are respectively designed to retain data records, the data records 21, 22, 24 and 26 thereof being designated in an exemplary manner. The data records retained in the lookup memory 19 together represent a lookup table and the data records retained in the lookup memory 20 together represent a lookup table. The look up memories 19 and 20 are each designed as random access memory and can in each case be formed by dynamic or static RAM (random access memory). The monitoring station 3 has a connection 28 for connecting the medical workstation 5, a connection 30 for connecting the medical workstation 7, and a connection 32 for a wired connection of the medical workstation 7. The connection 28 is connected to an interface 29 for receiving and sending data signals wirelessly. The connection 30 is connected to an interface 31 for sending and receiving a data signal wirelessly. The connection 32 is designed for the wired connection to a medical workstation and can be formed, for example, by a serial interface, in particular a USB interface.

The central processing unit 13 is connected to the memory 19 via a bidirectional data bus 35 and connected to the memory 20 via a bidirectional data bus 37 and said central processing unit is designed to read out at least one data record from the memory 19 via the bidirectional data bus 35 or to save a data record to the memory 19 via said bidirectional data bus. The central processing unit 13 can read out a data record from the memory 20 via the data bus 37 or save a data record to the memory 20 via the data bus 37.

The medical workstation 5 has an interface 39 for receiving and sending a data signal wirelessly. In this exemplary embodiment, the interface 39 can receive the data signal 82 sent wirelessly from the medical monitor 9 and the interface 11. The interface 39 is connected to an image rendering unit 41 of the medical workstation 5 via a connecting line 40. The image rendering unit 41 is connected to a respiratory device 43 via a connecting line 44. The respiratory device 43 has a connection 49 and a connection 51, which are respectively provided for connecting a respiratory tube. The respiratory device 43 is designed to generate a respiratory gas flow for ventilating a patient, e.g. the patient 4, and to acquire physiological data, particularly data relating to the respiration; to generate a data signal representing said data; and to send said data signal to the image rendering unit 41 via the connecting line 44. The respiratory device 43 has a radiofrequency detection device 45. The radiofrequency detection device 45 has a detection region 47 for a radiofrequency marker which extends in the region of the connection 49 for a respiratory tube 53. The respiratory tube 53 is designed to be connected to the connection 49 and has a radiofrequency marker 55 with marker information in the region of one tube end which is provided to be connected to the connection 49. The radiofrequency detection device 45 is designed to detect the radiofrequency marker 55—for example after connecting the tube end of the respiratory tube 53 into the connection 49—in the detection region 47 and to generate a marker signal which represents the marker information. The marker information can for example represent a serial number of the respiratory tube or an individual identification number which is provided for assignment to a patient. The marker information can also represent personal patient data. To this end, the radiofrequency marker 55 can have a random access memory which is designed to retain personal patient data. The respiratory device 43 is connected to the interface 39 via a connecting line 40 and can send the marker signal generated by means of the radiofrequency detection device 45 and/or a data signal representing the physiological respiratory data via the connecting line 40 to the interface 39. The interface 39 can send the received via the connecting line 40, the physiological data and/or the wirelessly sent data signal 82 to the monitoring station 3 as a wirelessly sent data signal 78. The wirelessly sent data signal 78 can be received by the interface 29 of the monitoring station 3. The connection 51 for a respiratory tube is provided for connecting the respiratory tube 57. In this exemplary embodiment, the respiratory tube 53 is provided for inspiration and the respiratory tube 57 for expiration.

The medical workstation 7 has a respiratory device 60, an image rendering unit 62, and an interface 64 for receiving a wirelessly sent data signal of another medical monitor. The interface 64 is connected to the respiratory device 60 via a connecting line 65. The respiratory device 60 has a connection 66 for wired connecting to the monitoring station 3. By way of example, it is possible for the connection 66 to be a USB connection. The respiratory device 60 has a radiofrequency detection device 68 with a detection region 70 for a radiofrequency marker which extends in the region of a connection 72 for a respiratory tube. The respiratory device 60 also has a connection 74 for a further respiratory tube. The respiratory device 60 is designed to generate a respiratory airflow for inspiration at the connection 72 and a respiratory airflow for expiration at the connection 74. The respiratory device 60 is connected on its output side to the image rendering unit 62 via a connecting line 75. The respiratory device 60 can acquire physiological respiration data, generate a data signal representing the latter, and send said data signal to the image rendering unit 62 via the connecting line 75. The respiratory device 60 can send an ECG data signal received by the interface 64 and/or a data signal representing the acquired physiological respiratory data to the monitoring station 3 via the connection 66.

The connection 32 of the monitoring station 3 is connected in a separable manner to the connection 66 of the medical workstation 7 via a connecting line 90. The connection 32 is connected to the central processing unit 13 via a connecting line 92. The connection 30 is connected to the central processing unit 13 via a connecting line 94, and the connection 28 is connected to said central processing unit 13 via a connecting line 96. The central processing unit is on its output side connected to the display unit 15 via a connecting line 98, and on its input side it is connected to the touch-sensitive surface 17 via a connecting line 99.

The touch-sensitive surface 17 is designed to generate a user interaction signal as a function of being touched, for example by a user hand 100, which signal represents a touch location of the touch on the touch-sensitive surface. The monitoring station 3 also has a keyboard 16 which is connected to the central processing unit 13 via a connecting line 97. The monitoring station 3 also has a radiofrequency programming device 69 which is designed to program and/or read out a radiofrequency marker in an effective range 67, and which is connected to the central processing unit 13 via a connecting line 93.

The functioning and interaction of the components of the medical system 1 will now be explained below:

The central processing unit 13 can acquire patient data, for example name, date of birth or patient data comprising the medical history of the patient, received via the keyboard 16 and save said data in the lookup memory 19 as patient data record 24 via the bidirectional data bus 35. The central processing unit can—for example as a function of a user interaction signal received via the connecting line 99—read out the patient data record 24 from the lookup memory 19 and send it to the radiofrequency programming device 69 via the connecting line 93. The radiofrequency programming device 69 can transfer the patient data record to a radiofrequency marker with a random access memory arranged in the effective range 67, and save said data record there as marker information. It is possible for the radiofrequency marker 55 of the respiratory tube 53 to have been programmed in this fashion.

The medical workstation 5 is connected to the monitoring station 3 via the interface 39, the interface 29 and the connection 28, and, there, to the central processing unit 13. When the respiratory tube 53 is connected to the connection 49 of the respiratory device 43, the radiofrequency detection device 45 of the respiratory device 43 can detect the radiofrequency marker 55 in the detection region 47 and generate a marker signal which represents the patient data previously programmed in the radiofrequency marker 55. The radiofrequency detection device 45 can send the marker signal, and hence the patient data, to the interface 39 via the connecting line 40. The interface can generate a data signal 78 which is sent wirelessly and which represents the marker signal and said interface can send the signal to the interface 29 of the monitoring station 3. The marker signal can thus be sent to the central processing unit 13 via the interface 29, the connection 28 and the connecting line 96.

The medical monitor 9, also referred to as an ECG monitor 9 in the following text, can acquire physiological data of the patient 4, in particular an electrocardiogram, and generate an ECG data signal representing the latter, and send said signal via the interface 11 to the medical workstation 5 and there to the interface 39. The medical workstation 5 can send physiological respiration data received via the connecting line 40 and/or the ECG data signal received from the ECG monitor 9 to the monitoring station 3 as a data signal 78 sent wirelessly via the interface 39. There, the wirelessly sent data signal 78 can be received wirelessly by the interface 29, and it is possible to generate a data signal which corresponds to said data signal and which can be received by the central processing unit 13 via the connection 28 and the connecting line 96. The central processing unit 13 can assign to the marker signal the data signal which represents the physiological data and temporally follows the previously received marker signal. To this end, the central processing unit 13 can read out a patient data record corresponding to the marker signal from the lookup memory 19 and can generate a data record representing the physiological data from the received data signal, and can save said data record as data record 26 in the lookup memory 26. The data record is assigned to the patient data record 24 in the lookup memory 19. In this manner, a fixed assignment of patient data and physiological data is retained in the lookup memory 19. The central processing unit 13 can read out the patient data record 24 and the data record 26 representing the physiological data from the lookup memory 19 via the bidirectional data bus 35 and can send them to the display unit 15 via the connecting line 98 and can render them together by means of the display unit 15. By way of example, the physiological data and the patient data can be rendered together in such a fashion that the physiological data are unambiguously assigned to the patient data. For example, the physiological data assigned to the patient data can be rendered in a row or in a column by means of the display unit 15.

The ECG monitor 9 is connected to a patient bed 10 by means of a holding device 8. By way of example, in the following text, the patient bed 10 can be transported to a different location together with the ECG monitor 9 and the patient 4. The respiratory tube 53 and the respiratory tube 57 can for example be connected to a mobile respiratory device 56 during transport. This makes it possible for the patient 4 to continue to be ventilated during transport as well. By way of example, the patient bed 10 can be transported to the medical workstation 7. By way of example, the medical workstation 7 can be arranged in another room of a hospital. The patient bed 10 is illustrated as patient bed 10', the holding device 8 as holding device 8', the ECG monitor 9 as ECG monitor 9', the interface 11 as interface 11', the patient 4 as patient 4', the respiratory tube 53 as respiratory tube 53', the respiratory tube 57 as respiratory tube 57' and the radiofrequency marker 55 as radiofrequency marker 55', respectively in the region of the medical workstation 7. If the respiratory tube 53' is connected to the connection 72 of the respiratory device 60, the radiofrequency detection device 68 can detect the radiofrequency marker 55' in the detection region 70 and generate a marker signal which represents the marker information and hence the patient data. The respiratory device 60 can send the marker signal to the monitoring station 3, via the connection 66, the connecting line 90, the connection 32 and the connecting line 92, and from there to the central processing unit 13. The central processing unit 13 can assign subsequently received data signals representing physiological data to the previously received marker signal. The medical workstation 7 can subsequently receive, via the interface 64, a wirelessly sent ECG data signal received by the interface 11' and representing an electrocardiogram. The interface 64 can generate a corresponding signal and send it to the respiratory device 60 via the connecting line 65. The respiratory device 60 can generate a data signal representing physiological data and send it, on the output side, together with the ECG data signal to the connection 32 of the monitoring station 3 via the connection 66 and the connecting line 90. The central processing unit 13 can receive the ECG data signal representing the physiological ECG data and the signal representing the physiological respiratory data via the connecting line 92 and assign them to the previously received marker signal. The central processing unit 13 can read out a patient data record 24 corresponding to the marker signal from the lookup memory 19 and can generate a data record 25 representing the corresponding physiological data and save said data record 25 in the lookup memory 19 via the connecting line 35. In this case, the data record 25 and the data record 26 are assigned to the patient data record 24. The data record 25 can be read out from the lookup memory 19 by the central processing unit 13, for example as a function of a user interaction signal received via the connecting line 99, together with the data record 24 and the data record 26 and can be sent to the display unit 15 via the connecting line 98 and can be output there respectively assigned to one another.

The central processing unit 13 can also receive a marker signal and a data signal representing the physiological data via the interface 31 and the connection 30. In this exemplary embodiment, the monitoring station 3 has a total of three connections for connecting a medical monitor. A monitoring station with a multiplicity of connections which are respectively designed for connecting a medical monitor is also feasible.

In this exemplary embodiment, the monitoring station 3 can, by means of the radiofrequency programming device 69, also detect a radiofrequency marker with marker information representing a serial number or an individual item of information of a respiratory tube. The central processing unit 13 can receive the corresponding marker signal via the connecting line 93 and generate a corresponding marker data record 21 and save this in the lookup memory 20 via the bidirectional data bus 37. The central processing unit 13 can for example generate a patient data record 22 and save this in the lookup memory 20 assigned to the marker data record 21, via the bidirectional data bus 37. The patient data record 22 can for example represent patient data received via the connecting line 97 or via the connecting line 99. In this fashion, it is possible for the monitoring station 3 to retain an unambiguous assignment of patient data and marker information of a radiofrequency marker, e.g. the radiofrequency marker 55. The central processing unit 13 can assign a marker signal received via the connecting line 96 or the connecting line 92 to the marker data record 21 read out from the lookup memory 20. To this end, the central processing unit 13 can read out the marker data records retained in the lookup memory 20, and compare them to the previously received marker signal. In the case of correspondence, the central processing unit 13 can generate a corresponding comparison result and read out the patient data record assigned to the corresponding marker data record and retained in the lookup memory 20 as a function of the comparison result. Thereupon the central processing unit 13 can save the patient data record in the lookup memory 19 via the bidirectional data bus 35 and save subsequently received physiological data assigned to said patient data record in the lookup memory 19. The lookup memories 19 and 20 can respectively be implemented by a combined memory. By way of example, it is possible that an assignment of a patient data record, a marker data record and a data record representing physiological data can be retained in a data structure. By way of example, the data structure can be formed by a database.

The central processing unit 13 can advantageously be controlled by a calculating program.

The interfaces 11, 29, 31 and 39 can in each case be a radio interface, a Bluetooth interface, a WLAN interface or an infrared interface.

FIG. 2 shows an exemplary embodiment of a method for assigning patient data to physiological data. In a method step 120, a radiofrequency marker 110 of a respiratory tube 108 is detected in a detection region 106 of a radiofrequency detection device 104 and a marker signal is generated which represents the marker information of the radiofrequency marker 110. In a further method step 122, the previously detected marker information is assigned to patient data. In a step 124, the radiofrequency marker 110 is detected at a position 110' in a detection region 118 of a radiofrequency detection device 114 of a respiratory device 112 and a marker signal representing the marker information is generated. In a further step 126, physiological data 126 are acquired and assigned to the marker information acquired in step 124. In a step 128, the physiological data acquired in step 126 are, as a function of the assignment carried out in step 126 and step 122, rendered together, in a fashion assigned to one another, together by means of a display unit.

The radiofrequency detection device 104 and the respiratory device 112 can be components of a medical system 102 (not illustrated in any more detail), which obtains physiological measurement data from medical monitors (not illustrated in any more detail).

LIST OF REFERENCE SYMBOLS

1 Medical system
3 Monitoring station
4, 4' Patient
5, 7 Medical workstation
8, 8' Holding device
10, 10' Patient bed
11, 11' Interface
13 Central processing unit
15 Display unit
16 Keyboard
17 Touch-sensitive surface
19, 20 Lookup memory
21, 22, 24, 26 Data record
28, 30, 32 Connection
29, 31, 39 Interface
35, 37 Data bus
41 Image rendering unit
43 Respiratory device
44 Connecting line
45 Radiofrequency detection device
47 Detection region
49, 51 Connection
53, 57 Respiratory tube
55 Radiofrequency marker
60 Respiratory device
62 Image rendering unit
64 Interface
66 Connection
67 Effective range
68 Radiofrequency detection device
69 Radiofrequency programming device
70 Detection region
72, 74 Connection
65, 75, 90, 92 Connecting line
93, 94, 96, 97 Connecting line
98, 99 Connecting line
100 Hand of a user
102 Medical system
104, 114 Radiofrequency detection device
106, 118 Detection region
108, 108' Respiratory tube
110, 110' Radiofrequency marker
112 Respiratory device
120, 122, 124 Step
126, 128 Step

The invention claimed is:

1. A medical system (1) with a monitoring station (3) and with at least one medical workstation (5, 7), the at least one medical workstation (5, 7) being designed to acquire physiological data of a patient and the at least one medical workstation (5, 7) being operatively connected to the monitoring station (3), and the at least one medical workstation (5, 7) being designed to generate a data signal representing the physiological data and to send said data signal to the monitoring station (3), the monitoring station (3) being designed to receive the data signal and having a memory (19, 20) for at least one patient data record (22, 24) representing the patient data and at least one display unit for displaying the physiological data (25, 26) and the patient data (22, 24), and the medical system being designed to assign the patient data (22, 24) and the physiological data (25, 26) to one another, wherein the at least one medical workstation (5, 7) has a respiratory device (43, 60) with a connection (49, 72) for a respiratory tube (53), and the medical workstation (5, 7) has a radiofrequency detection device (45, 68) which is designed to detect a radiofrequency marker (55) with marker information and to generate a marker signal representing the marker information, and the medical system (1) is designed to assign the physiological data (25, 26) and the patient data (22, 24) to one another, depending on the marker signal characterized in that the radiofrequency detection device (43, 60) is arranged to detect in the area of the connection for a respiratory tube a radiofrequency marker containing marker information and connected to the respiratory tube and to generate a marker signal representing the marker information, wherein the radiofrequency marker has a random access memory for the marker information and wherein the marker information represents the patient data, and in that the medical workstation is designed to generate a data record representing physiological data and to transfer this data record to and to save this data record in the radiofrequency marker by means of the radiofrequency detection device and to read out the data record representing physiological data by means of the radiofrequency detection device, whereby the medical workstation is able to carry out or continue a further operation depending on the read out of physiological data.

2. The medical system as claimed in claim 1, characterized in that at least one medical workstation (5, 7) is designed to transfer a data record representing adjustment or equipment parameters and save this data record in the radiofrequency marker of the respiratory tube.

3. The medical system as claimed in claim 2, characterized in that at least one medical workstation (5, 7) is designed to read out the data record (25, 26) which is saved in the radiofrequency marker (55) and represents the physiological data or adjustment or equipment parameters by means of the radiofrequency detection device (45, 68).

4. The medical system as claimed in claim 1, characterized in that at least one medical workstation (5) is connected wirelessly to the monitoring station (3).

5. The medical system as claimed in claim 1, characterized in that at least one medical workstation (7) is connected to the monitoring station (3) by wires.

6. A method of operating a medical system which includes at least one medical workstation, the method comprising:
 acquiring marker information of a respiratory tube;
 acquiring physiological data of a patient;
 assigning the physiological data to retained patient data depending on the marker information; and
 rendering the physiological data and patient data together, in particular visually or audibly, wherein the acquisition of the marker information includes detecting, in the area of a connection for a respiratory tube, a radiofrequency marker connected to a respiratory tube that contains marker information, and generating a marker signal representing the marker information, wherein the radiofrequency marker has a random access memory for the marker information, wherein the marker information represents the patient data, wherein the acquisition for the physiological data includes generating a data record representing physiological data and transferring this data record to and saving this data record in the radiofrequency marker and reading out the data record representing the physiological data, whereby the method is capable of carrying out or continuing a further operation of the at least one medical workstation depending on the read out physiological data.

7. The method as claimed in claim 6, characterized in that the marker information includes adjustment or equipment parameters generated individually for a patient.

8. The method claimed in claim 7, characterized in that operation can be continued at a different medical workstation using the adjustment or equipment parameters saved in the radiofrequency marker of the respiratory tube.

\* \* \* \* \*